(12) United States Patent
Abulhaj

(10) Patent No.: US 8,303,543 B2
(45) Date of Patent: Nov. 6, 2012

(54) BLOODLESS CATHETER AND NEEDLE SHIELDING CATHETER INSERTION APPARATUS

(76) Inventor: Ramzi Abulhaj, Miramar, FL (US)

( * ) Notice: Subject to any disclaimer, the term of this patent is extended or adjusted under 35 U.S.C. 154(b) by 1710 days.

(21) Appl. No.: 11/073,882

(22) Filed: Mar. 7, 2005

(65) Prior Publication Data

US 2006/0200080 A1    Sep. 7, 2006

(51) Int. Cl.
*A61M 5/178* (2006.01)
(52) U.S. Cl. ......... 604/164.01; 604/164.12; 604/167.03; 604/264; 606/167
(58) Field of Classification Search ............. 604/164.01, 604/164.012, 167.03, 167.04, 134–137, 264, 604/272, 523, 164.12; 600/433, 434, 435, 600/564, 567, 585; 606/167
See application file for complete search history.

(56) References Cited

U.S. PATENT DOCUMENTS

| | | | | |
|---|---|---|---|---|
| 5,704,911 | A | * | 1/1998 | Parsons ........................... 604/72 |
| 6,077,244 | A | * | 6/2000 | Botich et al. ................... 604/110 |
| 7,008,404 | B2 | * | 3/2006 | Nakajima ...................... 604/158 |

\* cited by examiner

*Primary Examiner* — Quynh-Nhu H Vu
(74) *Attorney, Agent, or Firm* — Clements Bernard PLLC; Christopher L. Bernard; Lawrence A. Baratta, Jr.

(57) ABSTRACT

An insertion apparatus, including an object for insertion into a patient; an insertion structure including an annular mounting structure having a mounting structure interior, the mounting structure containing a resilient membrane barrier extending across the mounting structure interior with a resiliently closing membrane opening for passing the object; so that the object can be inserted forwardly through the membrane opening and into a patient and subsequently withdrawn from the patient and rearwardly from the membrane opening, the membrane opening resiliently closes as the object exits the membrane opening and thereby preventing patient bodily fluid from flowing rearwardly out of the insertion structure.

7 Claims, 4 Drawing Sheets

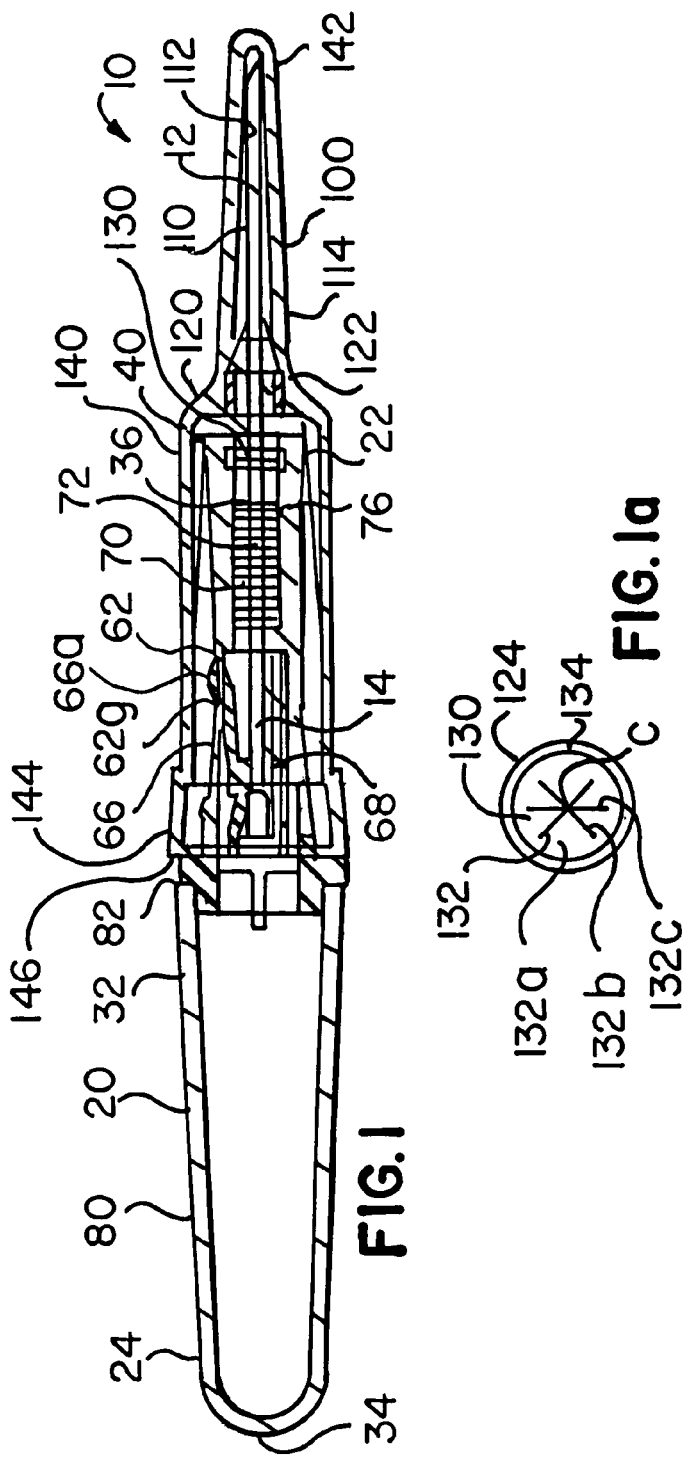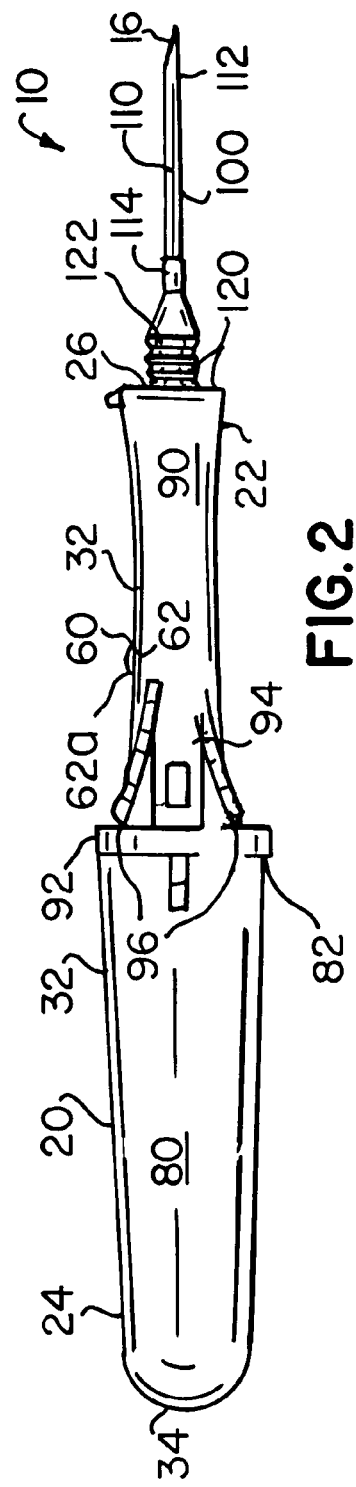

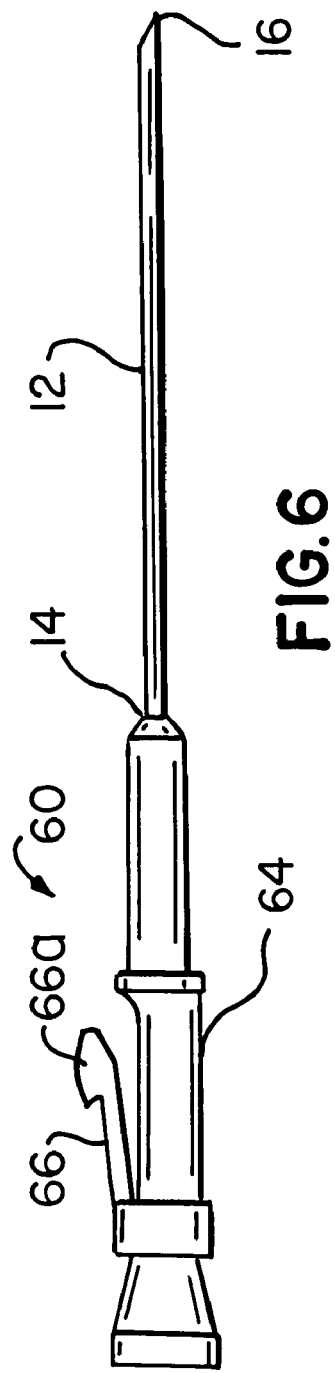
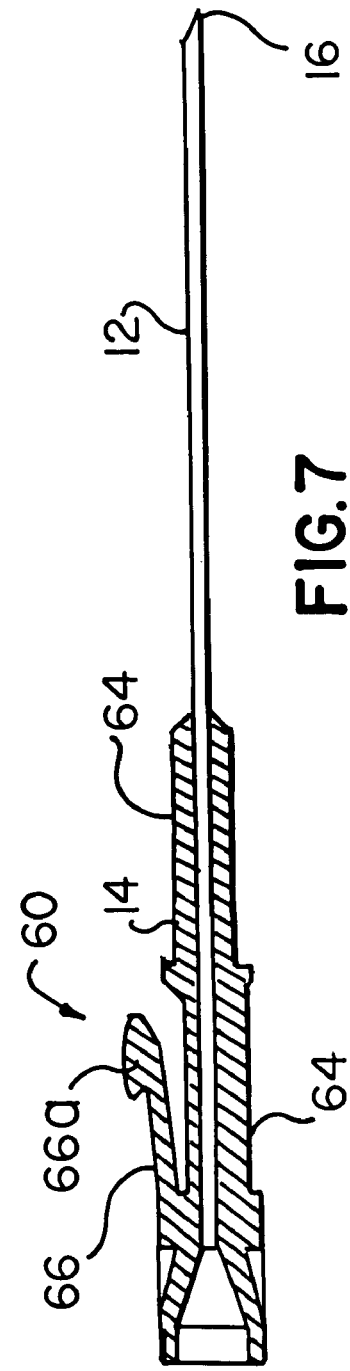

BLOODLESS CATHETER AND NEEDLE SHIELDING CATHETER INSERTION APPARATUS

BACKGROUND OF THE INVENTION

1. Field of the Invention

The present invention relates generally to the field of medication administration devices. More specifically the present invention relates to a catheter, or other object for insertion into the body of a patient, containing a perforated self-closing membrane barrier for preventing the escape of blood following object insertion, and to a catheter insertion apparatus having a catheter insertion needle which retracts into a needle containment housing.

The catheter includes a catheter tube having a catheter tube forward end and a catheter tube rearward end and an annular catheter mounting structure at the catheter tube rearward end including a catheter sleeve fitted over and fastened to the catheter tube rearward end and a catheter mounting hub containing the resilient membrane barrier extending across the hub interior with a self-closing membrane opening for passing a catheter insertion needle so that, as the needle is rearwardly withdrawn from the catheter following catheter insertion into a patient vein, the membrane opening resiliently closes as the needle exits and thereby prevents patient blood from flowing rearwardly out of the catheter, protecting medical personnel from contact with the patient blood. The membrane opening preferably is a pie-shaped cut including three cuts intersecting at a common central point in the membrane barrier, producing six radial cut segments extending at least part way toward the membrane perimeter. Although three intersecting cuts are preferred specifically, the preferred range is one to four intersecting cuts, while larger numbers of cuts are contemplated but are less preferred.

The catheter insertion apparatus includes a catheter insertion needle having a needle rearward end and a sharp needle forward end for removably fitting forwardly through the catheter so that the needle forward end protrudes forwardly of the catheter tube forward end for insertion of the needle forward end and catheter tube forward end into a vein of a patient. The apparatus further includes a needle containment housing for safely containing the needle after it is used, a needle containment housing, an annular catheter engaging structure formed on the needle containment housing for releasably engaging the catheter mounting structure, a needle cocking structure, and a needle retraction assembly for retracting the needle into the housing following catheter insertion.

2. Description of the Prior Art

There have been intravenous catheters for inserting into a patient vein and connecting to an intravenous line extending to a solution bag, and catheter insertion needles for fitting through the catheter so that the sharp forward end of the insertion needle protrudes from the catheter tube forward end to pierce the outer skin and vein of a patient and to guide the catheter tube forward end into the vein. A problem with these prior catheters has been that blood frequently spouts from the catheter as soon as the insertion needle is removed, exposing medical personnel to the many dangers of contaminated blood such as HIV. In addition the used insertion needle itself is contaminated with patient blood and presents a risk of infection through an accidental skin prick.

It is thus an object of the present invention to provide a bloodless catheter and needle shielding catheter insertion apparatus including an intravenous catheter having a membrane barrier which automatically blocks the escape of blood from the catheter following catheter insertion and needle removal.

It is a further object of the present invention to provide such a bloodless catheter and needle shielding catheter insertion apparatus in which the membrane barrier is formed of resilient material and is held in place between ends of two annular structures; in which the membrane has an opening including one or more cuts or slits for passing a catheter into the vein of a patient, and alternatively for passing a needle to withdraw blood from a patient vein, and for use in Central Venus Catheters procedures, which closes after removal of the needle from the membrane opening to preclude any blood flow through the membrane, and which has the ability to open and close in this way repeatedly.

It is a still further object of the present invention to provide such a bloodless catheter and needle shielding catheter insertion apparatus in which, when attaching an IV set, the cut or cuts in the membrane barrier open and thus permit the solution flow into a vein of a patient.

It is another object of the present invention to provide such a bloodless catheter and needle shielding catheter insertion apparatus which withdraws the catheter insertion needle from the catheter and into a housing to safely contain the insertion needle.

It is still another object of the present invention to provide such a bloodless catheter and needle shielding catheter insertion apparatus which prevents needle reuse.

It is finally an object of the present invention to provide such a bloodless catheter and needle shielding catheter insertion apparatus which is easy to use and economical to manufacture.

SUMMARY OF THE INVENTION

The present invention accomplishes the above-stated objectives, as well as others, as may be determined by a fair reading and interpretation of the entire specification.

A catheter insertion apparatus is provided, including a catheter including a catheter tube having a catheter tube forward end and a catheter tube rearward end and an annular catheter mounting structure at the catheter tube rearward end including a mounting structure interior, the catheter mounting structure containing a resilient membrane barrier extending across the mounting structure interior with a resiliently closing membrane opening for passing a catheter insertion needle; and a catheter insertion structure having a catheter insertion needle with a needle rearward end and with a needle forward end for removably fitting forwardly through the catheter so that the needle forward end protrudes forwardly from the catheter tube forward end to pierce patient skin and enter a patient vein together with the catheter tube forward end; and so that the catheter insertion needle can be rearwardly withdrawn from the catheter following catheter insertion into a patient vein, the membrane opening resiliently closing as the needle exits the membrane opening and thereby preventing patient blood from flowing rearwardly out of the catheter.

The catheter mounting structure preferably includes a mounting hub having a mounting hub interior containing the membrane barrier; and a catheter sleeve connected to the mounting hub and fitted over and fastened to the catheter tube rearward end. The membrane barrier has a membrane perimeter and the membrane opening preferably includes several cuts intersecting at a common point in the membrane barrier collectively defining a pie-shaped cut. The membrane opening preferably includes three cuts intersecting at a common point in the membrane barrier, defining six radial cut segments extending at least part way from the common point toward the membrane perimeter.

The catheter insertion structure preferably additionally includes a needle containment housing includes a tubular housing side wall and a housing rearward end with a housing rear wall sealingly joined to the housing side wall and a housing forward end with a housing opening; and a needle cocking structure and an annular catheter engaging structure connected to the needle containment housing forward end for releasably engaging the catheter mounting structure.

The apparatus preferably additionally includes a needle retraction assembly including a spring abutment structure connected to and contained within the housing; where the annular catheter engaging structure is connected adjacent to the housing opening. The needle cocking structure preferably is mounted to the needle rearward end, and the retraction assembly preferably includes a needle retraction spring and having a spring rearward end for bearing against the needle cocking structure and having a spring forward end for bearing against the spring abutment structure. The needle retraction spring preferably includes a coil spring encircling the needle.

The needle cocking structure preferably includes a trigger slot in the housing side wall extending rearwardly-to-forwardly and having a trigger slot rearward edge, a needle sleeve fitted over and fastened to the needle rearward end; and a resilient locking arm secured to the needle sleeve and extending forwardly and resiliently outward from the needle sleeve to an arm free end, the locking arm having a locking trigger barb at the arm free end releasably engaging the trigger slot rearward edge in the housing side wall; so that the insertion needle is initially positioned forwardly relative to the needle containment housing to an extent that the needle forward end protrudes from the housing forward end a distance greater than the length of the catheter tube to protrude forwardly of the catheter tube forward end, and so that manually depressing the locking barb into the housing until the locking barb slides off the trigger slot edge dislodges the trigger barb and thus frees the needle to accelerate rearwardly within the housing with the biasing of the needle retraction spring to prevent used needle pricks and to prevent reuse of the insertion apparatus.

BRIEF DESCRIPTION OF THE DRAWINGS

Various other objects, advantages, and features of the invention will become apparent to those skilled in the art from the following discussion taken in conjunction with the following drawings, in which:

FIG. 1 is a cross-sectional side view of the preferred embodiment of the entire apparatus including the catheter cover, with the needle retraction assembly in its cocked position.

FIG. 1a is a cross-sectional end view of the catheter mounting hub showing the membrane barrier and preferred membrane opening including three intersecting cuts.

FIG. 2 is a side view of the apparatus as in FIG. 1 with the catheter cover removed.

FIG. 6 is a side view of the combined needle, needle sleeve and locking arm.

FIG. 7 is a cross-sectional side view of the combined needle, needle sleeve and locking arm as shown in FIG. 6.

DETAILED DESCRIPTION OF THE PREFERRED EMBODIMENTS

Figure 1B:
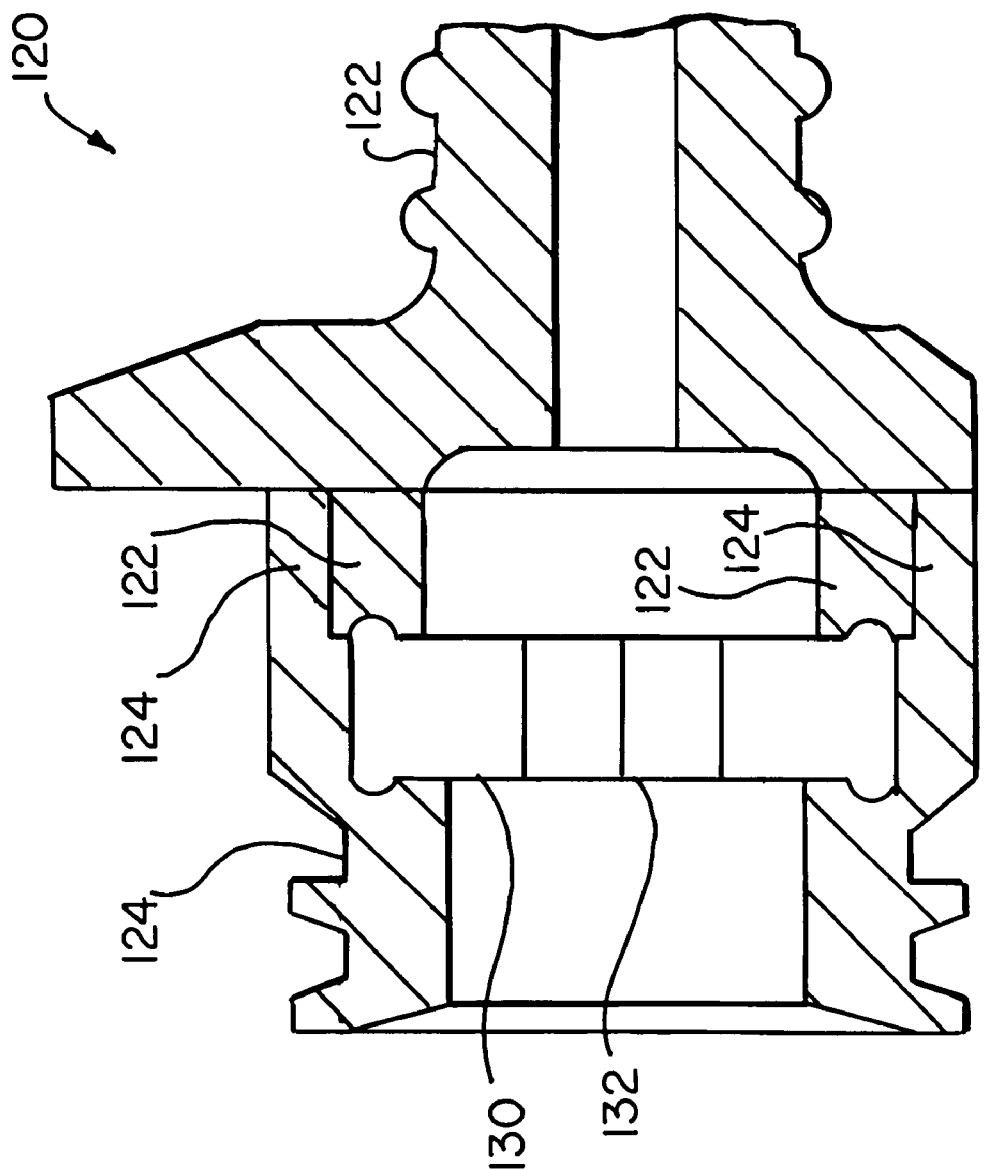
FIG. 1b is a close-up cross-sectional side view of the annular catheter mounting structure and catheter sleeve showing that they are separate parts, and showing the preferred way in which the membrane barrier is mounted and retained between the catheter mounting structure and catheter sleeve.

As required, detailed embodiments of the present invention are disclosed herein; however, it is to be understood that the disclosed embodiments are merely exemplary of the invention which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Reference is now made to the drawings, wherein like characteristics and features of the present invention shown in the various figures are designated by the same reference numerals.

First Preferred Embodiment

Figure 3:
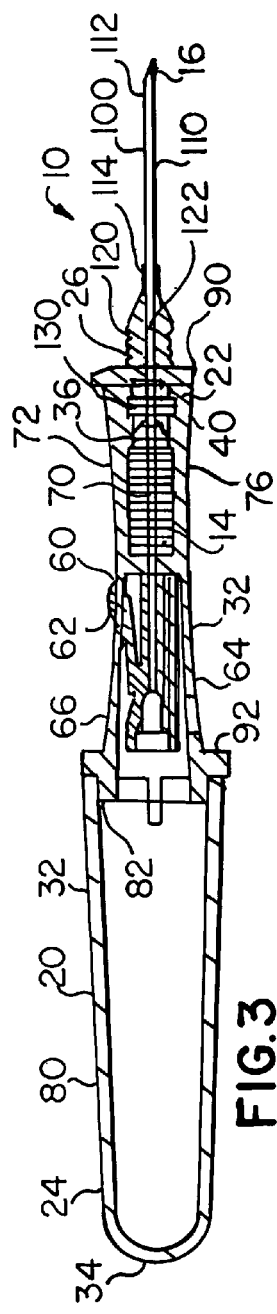
FIG. 3 is a cross-sectional side view of the apparatus as in FIG. 1 with the catheter cover removed.
Figure 4:
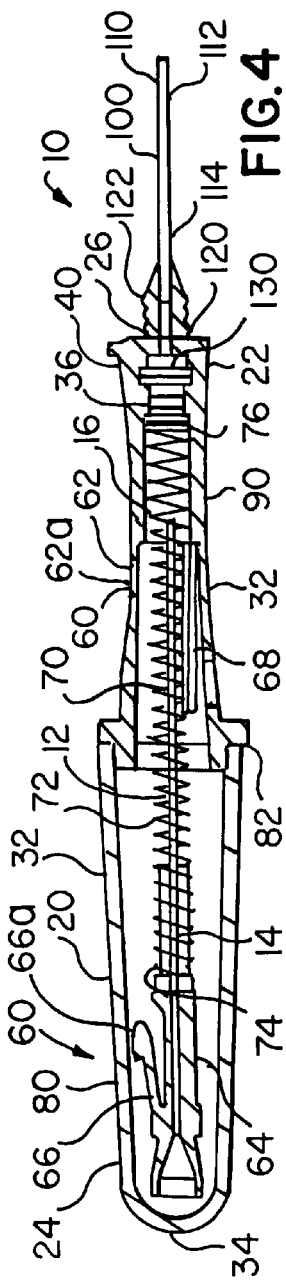
FIG. 4 is a cross-sectional side view of the apparatus as in FIG. 3, but showing the needle retraction assembly in its fired position and the insertion needle safely contained within the needle containment housing.
Figure 5:
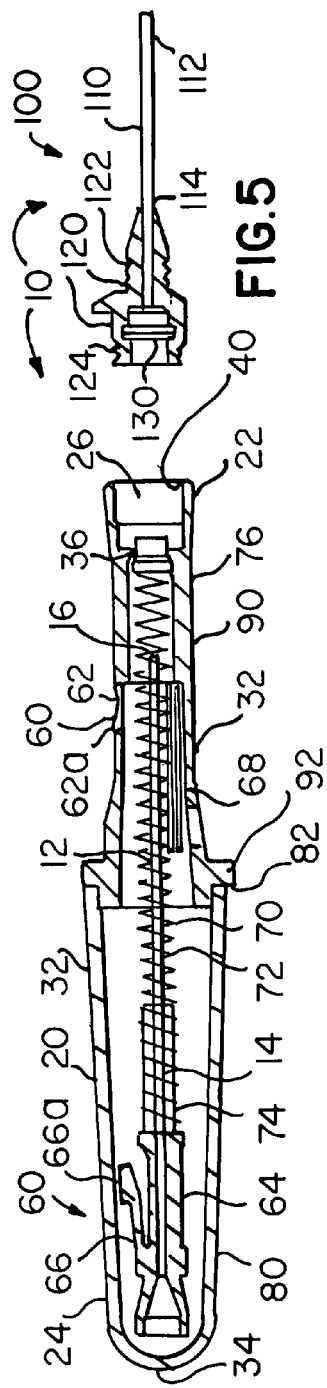
FIG. 5 is a view as in FIG. 4 except that the catheter is shown removed from the containment housing in forwardly exploded relation.

Referring to FIGS. 1-7, a catheter insertion apparatus 10 and catheter 100 are disclosed, the catheter 100 including a a catheter tube 110 having a catheter tube forward end 112 and a catheter tube rearward end 114 and an annular catheter mounting structure 120 at the catheter tube rearward end 114 including a catheter sleeve 122 fitted over and fastened to the catheter tube rearward end 114 and a catheter mounting hub 124 integral with the catheter sleeve 122 and containing a resilient membrane barrier 130 extending across the hub interior with a self-closing membrane opening 132 for passing a catheter insertion needle 12 so that, as the needle 12 is rearwardly withdrawn from the catheter 100 following catheter 100 insertion into a patient vein, the membrane opening 132 resiliently closes as the needle 12 exits and thereby prevents patient blood from flowing rearwardly out of the catheter 100, protecting medical personnel from contact with the patient blood. The membrane opening 132 preferably has the ability to open and close in this way repeatedly. The membrane opening 132 preferably is a pie-shaped cut including three cuts 132a, 132b and 132c intersecting at a common central point C in the membrane barrier 130, producing six radial cut segments extending at least part way toward the membrane perimeter 134. Although three intersecting cuts are preferred specifically, the preferred number of intersecting cuts is one to four cuts. Larger numbers of intersecting cuts are contemplated but are less preferred, as are non-intersecting cuts.

The catheter insertion apparatus 10 includes a catheter insertion needle 12 having a needle rearward end 14 and a sharp needle forward end 16 for removably fitting forwardly through the catheter 100 so that the needle forward end 16 protrudes forwardly of the catheter tube forward end 112 for insertion of the needle forward end 14 and catheter tube forward end 112 into a vein of a patient. The apparatus 10 further includes a needle containment housing 20 for safely containing the needle after it is used, a needle containment housing 20, an annular catheter engaging structure 40 formed on the needle containment housing 20 for releasably engaging the catheter mounting structure 120, a needle cocking structure 60, and a needle retraction assembly for retracting the needle into the housing 20 following catheter 100 insertion.

The needle containment housing 20 has a housing forward end 22 with a housing opening 26 and has a tubular housing side wall 32 and a housing rearward end 24 with a housing rear wall 34 sealingly joined to the housing side wall 32 and contains the retraction assembly 70 which includes a spring abutment structure 36 formed as part of the housing 20. The annular catheter engaging structure 40 is formed as part of and encircles the housing opening 26.

The needle cocking structure 60 is mounted to the needle rearward end 14, and the retraction assembly 70 includes a needle retraction spring 72 in the form of a coil spring encircling the needle 12 and having a spring rearward end 74 for bearing against the needle cocking structure 60 and having a spring forward end 76 for bearing against the spring abutment structure 36.

The needle cocking structure 60 preferably includes a trigger slot 62 in the housing side wall 32 forward end extending rearwardly to forwardly and having a slot rearward edge 62a, and includes a needle sleeve 64 fitted snugly over and fastened to the needle rearward end 14 such as with an adhesive, and a resilient locking arm 66 extending forwardly and resiliently protruding outwardly from the needle sleeve 64. The locking arm 66 has a locking trigger barb 66a at the arm free end releasably engaging the slot rearward edge 62a. A needle sleeve abutment structure 68 preferably protrudes from housing side wall 32 inwardly opposite the trigger slot 62 to abut and hold in position the needle sleeve 64 while manual pressure is applied to the trigger barb 66a.

Initially the insertion needle 12 is positioned forwardly relative to the needle containment housing 20 so that the needle forward end 16 protrudes from the housing forward end 22 a distance greater than the length of the catheter tube 110 to protrude forwardly out of the catheter tube 110. Manually depressing the locking barb 66a inwardly so that it slides off the trigger slot edge 62a dislodges the trigger barb 66a and thus frees the needle cocking structure 60 and needle 12 to accelerate rearwardly within the housing 20 with the biasing of the needle retraction spring 72 to prevent both used needle 12 pricks and the reuse of the catheter insertion apparatus 10.

The needle containment housing 20 preferably is formed as a separate housing forward portion 90 and housing rearward portion 80 so that the needle cocking structure 60 can be inserted into the housing forward portion 90 and the housing forward and rearward portions 90 and 80 respectively then bonded together. The housing rearward portion 80 has a rearward portion rim 82 and the housing forward portion 90 has a radial stop flange 92 spaced a short distance forwardly from the housing forward portion 90 rearward end for abutting the rearward portion rim 82 when the housing forward portion 90 rearward end is inserted into the housing rearward portion 80.

Radial fins 94 preferably extend outward from the housing forward portion 90 rearward segment and have fin notches 96 at the radial fin 94 rearward ends. A tubular catheter cover 140 preferably is provided having a closed cover forward end 142 and an open cover rearward end 144 with an inward engaging bead 146. The catheter cover 140 fits over the housing forward end 90 and the engaging bead 146 removably engages the fin notches 96 to hold the catheter cover 140 in place over the housing forward end 90 until the catheter cover 140 is manually removed.

While the invention has been described, disclosed, illustrated and shown in various terms or certain embodiments or modifications which it has assumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

I claim as my invention:

1. A catheter insertion apparatus, comprising:

a catheter comprising a catheter tube having a catheter tube forward end and a catheter tube rearward end and an annular catheter mounting structure at said catheter tube rearward end comprising a mounting structure interior, said catheter mounting structure containing a resilient membrane barrier extending across the mounting structure interior with a self-closing membrane opening, wherein said membrane opening is opened for passing a catheter insertion needle;

a catheter insertion catheter insertion structure having a catheter insertion needle with a needle rearward end and with a needle forward end for removably fitting forwardly through said catheter such that said needle forward end protrudes forwardly from said catheter tube forward end to pierce patient skin and enter a patient vein together with said catheter tube forward end;

and such that said catheter insertion needle can be rearwardly withdrawn from said catheter following catheter insertion into a patient vein, said self-closing membrane opening resiliently closing as said needle exits said membrane opening and thereby preventing patient blood from flowing rearwardly out of said catheter;

a needle retraction assembly comprising a spring abutment structure connected to and contained within said housing;

wherein said annular catheter engaging structure is connected adjacent to said housing opening;

wherein said catheter insertion structure additionally comprises:

a needle containment housing comprising a tubular housing side wall and a housing rearward end with a housing rear wall sealingly joined to said housing side wall and a housing forward end with a housing opening;

and a needle cocking structure and an annular catheter engaging structure connected to said needle containment housing forward end for releasably engaging said catheter mounting structure, wherein said needle cocking structure is mounted to said needle rearward end, and said retraction assembly comprises a needle refraction spring and having a spring rearward end for bearing against said needle cocking structure and having a spring forward end for bearing against said spring abutment structure.

2. The apparatus of claim 1, wherein said catheter mounting structure comprises:

a mounting hub having a mounting hub interior containing said membrane barrier;

and a catheter sleeve connected to said mounting hub and fitted over and fastened to said catheter tube rearward end.

3. The apparatus of claim 1, wherein said membrane barrier having a membrane perimeter and wherein said membrane opening comprises a plurality of cuts intersecting at a common point in said membrane barrier collectively defining a pie-shaped cut.

4. The apparatus of claim 1, wherein said membrane opening comprises three cuts intersecting at a common point in said membrane barrier, defining six radial cut segments extending at least part way from the common point toward said membrane perimeter.

5. The apparatus of claim 1 wherein said needle retraction spring comprises a coil spring encircling said needle.

6. The apparatus of claim 1, wherein said needle cocking structure comprises:
- a trigger slot in said housing side wall extending rearwardly-to-forwardly and having a trigger slot rearward edge,
- a needle sleeve fitted over and fastened to said needle rearward end; and
- a resilient locking arm secured to said needle sleeve and extending forwardly and resiliently outward from said needle sleeve to an arm free end, said locking arm having a locking trigger barb at said arm free end releasibly engaging said trigger slot rearward edge in said housing side wall;
- such that said insertion needle is initially positioned forwardly relative to said needle containment housing to an extent that said needle forward end protrudes from said housing forward end a distance greater than the length of said catheter tube to protrude forwardly of said catheter tube forward end, and such that manually depressing said locking barb into said housing until said locking barb slides off said trigger slot edge dislodges said trigger barb and thus frees said needle to accelerate rearwardly within said housing with the biasing of said needle retraction spring to prevent used needle pricks and to prevent reuse of said insertion apparatus.

7. A catheter insertion apparatus for inserting a catheter comprising a catheter tube having a catheter tube forward end and catheter tube rearward end and an annular catheter mounting structure at the catheter tube rearward end, comprising:
- a catheter insertion needle with a needle rearward end and with a needle forward end for removably fitting forwardly through the catheter such that said needle forward end protrudes forwardly from the catheter tube forward end to pierce patient skin and enter a patient vein together with the catheter tube forward end;
- wherein said catheter mounting structure comprises a mounting hub and a catheter sleeve connected to said mounting hub and fitted over and fastened to the catheter tube rearward end;
- wherein said catheter insertion structure additionally comprises a needle containment housing comprising a tubular housing side wall and a housing rearward end with a housing rear wall sealingly joined to said housing side wall and a housing forward end with a housing opening, and a needle cocking structure and an annular catheter engaging structure connected to said needle containment housing forward end for releasibly engaging said catheter mounting structure;
- a needle retraction assembly comprising a spring abutment structure connected to and contained within said housing, wherein said annular catheter engaging structure is connected adjacent to said housing opening;
- wherein said needle cocking structure is mounted to said needle rearward end, and said retraction assembly comprises a needle retraction spring having a spring rearward end for bearing against said needle cocking structure and having a spring forward end for bearing against said spring abutment structure;
- wherein said needle retraction spring comprises a coil spring encircling said needle;
- and wherein said housing side wall comprises a trigger slot extending rearwardly-to-forwardly and having a trigger slot rearward edge; a needle sleeve fitted over and fastened to said needle rearward end; and a resilient locking arm secured to said needle sleeve and extending forwardly and resiliently outward from said needle sleeve to an arm free end, said locking arm having a locking trigger barb at said arm free end releasibly engaging said trigger slot rearward edge in said housing side wall;
- such that said insertion needle is initially positioned forwardly relative to said needle containment housing to an extent that said needle forward end protrudes from said housing forward end a distance greater than the length of said catheter tube to protrude forwardly of said catheter tube forward end, and such that manually depressing said locking barb into said housing until said locking barb slides off said trigger slot edge dislodges said trigger barb and thus frees said needle to accelerate rearwardly within said housing with the biasing of said needle retraction spring to prevent used needle pricks and to prevent reuse of said insertion apparatus.

\* \* \* \* \*